United States Patent [19]

Katagiri

[11] 4,277,238
[45] Jul. 7, 1981

[54] ARTIFICIAL BONELIKE GRAFT AND METHOD FOR PRODUCING THE SAME

[76] Inventor: Masataka Katagiri, 2398-2 Sakai, Niigata-shi, Niigata, Japan

[21] Appl. No.: 25,730

[22] Filed: Mar. 30, 1979

[30] Foreign Application Priority Data

Sep. 28, 1978 [JP] Japan ............................. 53/120618

[51] Int. Cl.³ ........................................... A01N 35/02
[52] U.S. Cl. ................... 433/201; 128/92 G; 424/334; 3/1.9; 422/36; 422/40
[58] Field of Search ...................... 424/334, 315; 34/5; 433/201; 422/36, 40; 128/92 G, 1 R; 3/1.9

[56] References Cited
U.S. PATENT DOCUMENTS

| | | | |
|---|---|---|---|
| 2,347,567 | 4/1944 | Kresse | 424/334 |
| 3,126,884 | 3/1964 | Tucker, Jr. | 128/92 G |
| 3,127,317 | 3/1964 | Kern | 34/5 |
| 3,573,082 | 3/1971 | Fremling | 424/334 |

*Primary Examiner*—Norman Yudkoff
*Attorney, Agent, or Firm*—Koda and Androlia

[57] ABSTRACT

An artificial bonelike graft is disclosed. The graft of this invention comprises a biological material such as a bone piece and tooth taken from an animal or a human, which material is decalcified and defatted. Upon implanting the graft, it will be assimilated with the existing tissues and become a part of the living organs. A method for producing such grafts is also disclosed.

13 Claims, 3 Drawing Figures

ARTIFICIAL BONELIKE GRAFT AND METHOD FOR PRODUCING THE SAME

BACKGROUND OF THE INVENTION

1. Field of the Invention

This invention relates to an artificial bonelike graft and more particularly to an artificial bonelike graft made of a biological material and a method for producing the same.

2. Prior Art

In general, artificial bonelike grafts such as false teeth and false bone pieces are made of non-biological material. However, non-biological materials are not satisfactory in terms of the lack of assimilability to existing tissues of a human body. More specifically the surrounding living organs will likely present rejection symptoms against such artifical grafts causing the implantation unstable or unpleasant.

A number of attempts have been made to improve the implantation of those artifical bonelike grafts. However, none of them has ever succeeded in overcoming rejection symptoms by existing human tissues.

SUMMARY OF THE INVENTION

Accordingly, it is the primary object of this invention to provide an artificial bonelike graft made of biological materials which overcomes all the shortcomings that the prior art graft has failed to solve.

It is another object of this invention to provide an artificial bonelike graft which can be assimilated with the living organs.

It is still another object of this invention to provide a method for producing an artificial bonelike graft made of biological material.

In keeping with the principles, the objects of this invention are accomplished by an artificial bonelike graft made of decalcified and defatted biological materials such as a tooth and a bone piece taken from animals.

DETAILED DESCRIPTION OF THE INVENTION

This invention will be best understood by describing an embodiment of a method for producing an artifical bone piece of this invention at first.

A piece of long bone is taken from a fresh animal body. The bone piece is then chemically treated with a fixation agent such as formaldyhyde, alcohol and the like. The fixing may take about twenty-four hours or longer depending upon the type of animal. As the fixing agent, in addition to formalin and alcohol, paraformaldehyde may be used for smaller pieces. To obtain the best results, 5-30% formalin may be used. It is further preferable to use about 10% formalin. At above 30% or below 5% the protein contained in the bone piece may be deteriorated.

Immediately following the fixation step, the bone piece is decalcified with a decalcifying agent such as an acid and ethylenediaminetetraacetate acetate. The acid may preferably be selected from the group comprising formic acid, hydrochloric acid, oxalic acid and citric acid. The acid may preferably be in 3-10%. Above 10%, the bone piece may have corrosion, and below 3% the piece may not be decalcified sufficiently.

After the decalcifying step, the bone piece is defatted with a defatting agent such as alcohol to sterilize the same. The alcohol may preferably be selected from the group consisting of ethyl alcohol and butyl alcohol. The alcohol may preferably be in 50-80%.

Following the defatting step, the bone piece is washed with and dehydrated with alcohol such as ethyl alcohol.

Then the bone piece is freeze dried at preferably below 4° C.

The bone piece may be kept either as in the original shape or as powder.

In addition to the above embodiment, a number of variations may be used.

Finally, instead of bone piece, a tooth may be processed in the same fashion. The type of animal is not limited; however, it is preferable to use an animal which has a similar bone structure to the object which is to receive treatment. Therefore, if a human being is to receive treatment, a mammal is preferably used.

The steps of decalcifying and defatting may be executed in any order. Those two steps may even be executed in a single step by applying a decalcifying agent at first and then applying a defatting agent. In case an alcohol is used as a fixing agent, the defatting step can be executed at the same time by the same alcohol, thereby saving a step.

Before applying a bone piece thus processed, the piece may be treated with a sterilizing agent such as antibiotics.

Now referring to the attached drawings, there is given an example of implantation of a graft of this invention.

Figure 1A:
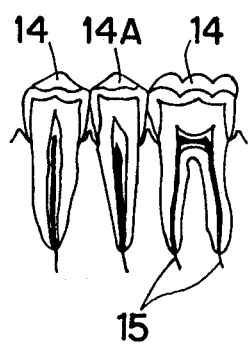
FIGS. 1 (A)-(E) show cross-section views illustrating the steps of implantation where a tooth of a rabbit with a healthy periodontal membrane is replaced with an artificial bonelike graft of this invention.
Figure 1B:
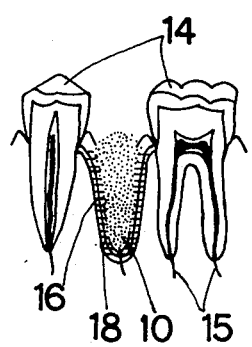
Figure 1C:
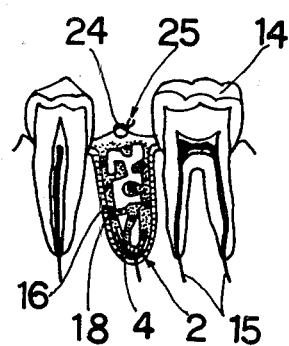
Figure 1D:
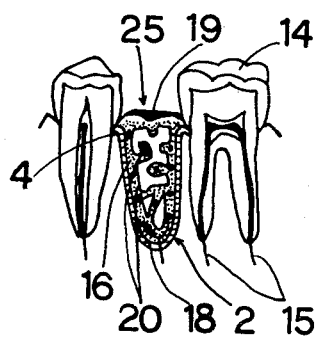
Figure 1E:
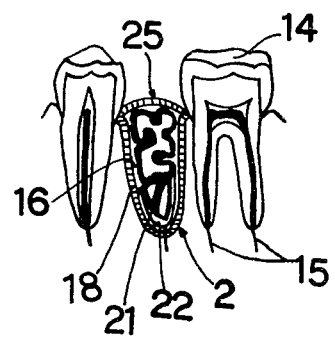

First referring to FIGS. 1 (A)-(E), there is shown a series of steps of implanting a graft into a canine extraction hole of a rabbit which has a healthy periodontal membrane. The graft used in this embodiment is made of a piece of long bone of a mouse which is fixed with 10% formalin decalcified with 5% formic acid, defatted with 70% alcohol and freeze dried.

FIG. 1 (A) shows a cross-section view of a series of teeth, 14 including a canine tooth to be extracted. The reference numeral 15 designates a blood tube and nerve tissue.

FIG. 1 (B) shows a cross-section view of the teeth 14 where a canine tooth is extracted. The hole 16 is filled with blood clot 10. The periodontal membrane 18 is left in the hole 16.

FIG. 1 (C) shows a cross-section view of the teeth 14 where the graft 2 is inserted into the hole 16 and the surface 25 of the hole 16 is sutured with a suture thread 24 which is also made of a biological material. At this stage, the graft 2 is surrounded by blood clot 10.

FIG. 1 (D) shows a cross-section view of the teeth 14 where the blood clot 10 is replaced with granulation tissue 20. The pores of the graft 2 are filled with osteoblast and chondroblast. At this stage there is generated some new bone tissue around the graft 2 and the surface 25 of the hole is covered with crust.

FIG. 1 (E) shows a cross-section of teeth 14 after approximately one month where the graft 2 has become calcified and there is regenerated a new periodontal membrane 18 between the graft 2 and the wall 22 of the hole 16. Thus, the graft 2 has thoroughly become a part of the existing organ.

Figure 2A:
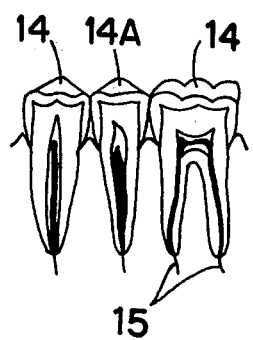
FIGS. 2 (A)-(E) show cross-section views illustrating the steps of implantation where a tooth of a rabbit with an unhealthy periodontal membrane is replaced with an artificial bonelike graft of this invention.
Figure 2B:
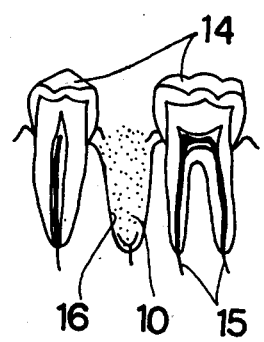
Figure 2C:
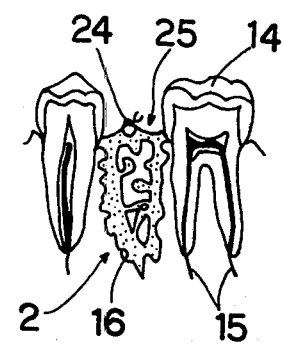
Figure 2D:
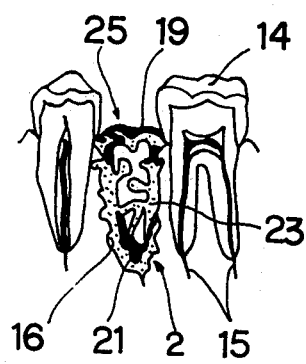
Figure 2E:

FIGS. 2(A)-(E) shows another example where the same treatment is performed except that the periodontal membrane is not healthy. The implantation may be operated in the same manner. As shown in FIG. 1 (E), there is no regeneration of the membrane between the graft 2 and the wall 22 of the hole. However, the graft 2 has become a part of the existing organ as in the first example.

Figure 3A:
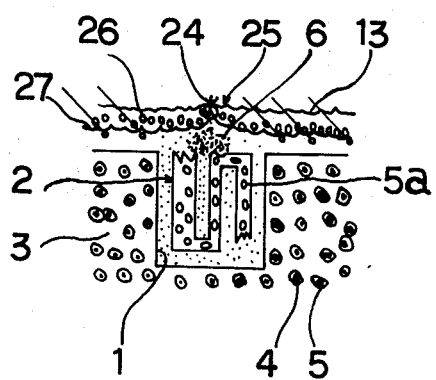
FIGS. 3 (A)-(D) show cross-section views illustrating the steps of implantation where a cavity in a bone structure of a rabbit is filled with an artificial bonelike graft of this invention.
Figure 3B:
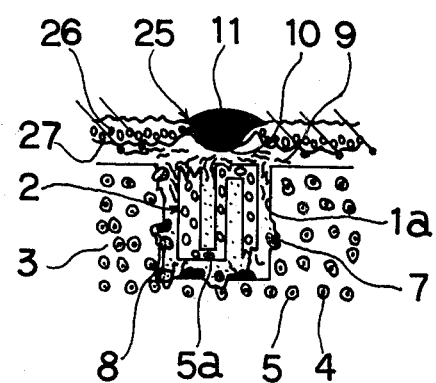
Figure 3C:
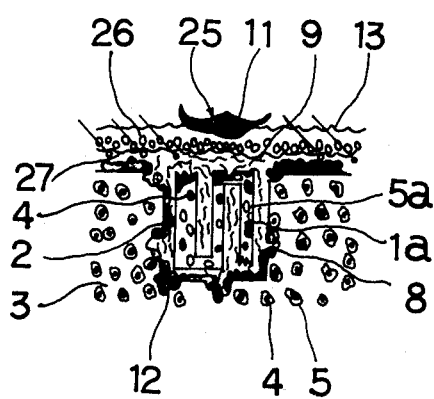
Figure 3D:
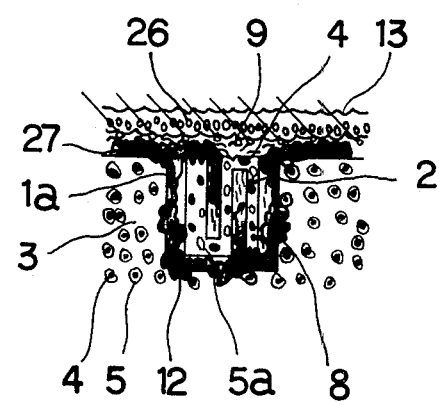

FIGS. 3 (A)-(E) shows still another example of the implantation of a bone graft of this invention. In this example, the same type of graft as in the previous examples is implanted into a cavity provided in a coccyx of a mouse.

FIG. 3 (A) shows a cross-section view of a coccyx bone structure where there is provided a cavity 1 into which a graft 2 of this invention is inserted. In the bone tissue 3 there exist osteocytes, chondrocytes and osteoblast 4 and 5. On the other hand, there is no such substances in lacunae 5a of the graft 2. There is seen some blood 6 getting blood clot between the cavity and the graft 2 and also in the lacunae 5a of the graft 2.

FIG. 3 (B) shows a stage where some polykaryocyte (osteoclast) 7 is generated on the cavity wall 1a; however, ther is no rejection symptom at the graft 2. The graft 2 has obtained some fibroblasts 9 thereon. The surface 25 is covered with blood clot 10 and crust 11.

FIG. 3 (C) shows the third stage after approximately three weeks where there is generated some new bone tissue 12 around the polykaryocyte 7 extending toward the graft 2. At this stage, in the lacunae 5a of the graft 2 some bone tissue 3 and chondroblast 4 have entered. The graft 2 has slowly started getting calcified.

FIG. 3 (D) shows the fourth stage after approximately one month, where the graft 2 is calcified and the raw bone tissue 12 generated on the cavity wall 1a has become an integral part of the coccyx of the mouse by fibroblasts, chondroblasts and osteoblast the surface 25 is thoroughly cured and covered with surface skin 13. The numeral 26 designates epitherial cells and 27 designates epitherium.

In case a graft to be inserted is not treated as in this invention, the organ will suffer from suppurative inflammation resulting in exclusion of such graft.

In contrast, according to this invention, although the graft implantation may cause slight chronic inflammation around the graft whose pores are filled with blood clot, the graft will be surrounded by granulation and the inflammation will diminish. In a month adhesion will start between the graft and the existing organ. In six months, the graft will become an integral part of the organ.

Thus, the graft of this invention functions as a proper spacer as it is implanted into a cavity and also as a strong foundation for inserting a false tooth without causing rejection symptoms. In addition, if a suture thread made of a biological material is used, it is even unnecessary to remove the thread, since it is absorbed into the living organs.

I claim:
1. A method for producing an artificial bonelike graft comprising the steps of:
   (a) fixing a bonelike piece taken from a mammal with a fixing agent selected from the group consisting of formalin, alcohol and paraformaldehyde,
   (b) decalcifying said piece with a decalcifying agent comprising an acid selected from the group consisting of formic acid, hydrochloric acid, nitric acid, oxalic acid and citric acid,
   (c) defatting said piece with alcohol, and
   (d) freeze drying said piece.
2. A method for producing an artificial bonelike graft according to claim 1, wherein before said freeze drying step, said piece is washed with water and dehydrated with alcohol.
3. A method for producing an artificial bonelike graft comprising the steps of:
   (a) fixing a bonelike piece taken from a mammal with a fixing agent selected from the group consisting of formalin, alcohol and paraformaldehyde,
   (b) decalcifying said piece with a decalcifying agent selected from the group consisting of formic acid, hydrochloric acid, nitric acid, oxalic acid, citric acid, and ethylenediaminetetraacetate,
   (c) defatting said piece with alcohol, and
   (d) freeze drying said piece.
4. The method of claim 3 wherein said bonelike graft is a biological material selected from the group consisting of bone and teeth.
5. The method of claim 3 wherein prior to said freeze drying step, said piece is washed with water and dehydrated with alcohol.
6. The method of claim 3 wherein said fixing agent is formalin and is diluted to a strength from 5% to 30%.
7. The method of claim 3 wherein said decalcifying agent is an acid and is diluted to a strength from 3% to 10%.
8. The method of claim 3 wherein said alcohol used in said defatting step is selected from the group consisting of ethyl alcohol and butyl alcohol, and is diluted to a strength from 50% to 80%.
9. The method of claim 3 wherein said defatting step (c) is performed subsequent to said decalcifying step (b).
10. The method of claim 3 wherein said defatting step (c) is performed prior to said decalcifying step (b).
11. The method of claim 3 wherein said defatting step (c) is performed simultaneously with said fixing step (a) and wherein said fixing agent is alcohol.
12. The method of claim 3 comprising the further step of:
   (e) treating said piece with an antibacterial sterilizing agent.
13. A method for producing an artificial bonelike graft from a biological material selected from the group consisting of bone and teeth comprising the steps of fixing the material with 5% to 30% formalin, decalcifying the material with 3% to 10% acid, defatting the material with 50% to 80% alcohol and freeze drying the material at below 4° C.

* * * * *